(12) United States Patent
Cocks et al.

(10) Patent No.: US 7,200,203 B2
(45) Date of Patent: Apr. 3, 2007

(54) DEVICES AND METHODS FOR TARGETING INTERIOR CANCERS WITH IONIZING RADIATION

(75) Inventors: Franklin H. Cocks, Durham, NC (US); Walter Neal Simmons, Durham, NC (US); Paul A. Klenk, Wilmette, IL (US)

(73) Assignee: Duke University, Durham, NC (US)

( * ) Notice: Subject to any disclaimer, the term of this patent is extended or adjusted under 35 U.S.C. 154(b) by 238 days.

(21) Appl. No.: 10/818,593

(22) Filed: Apr. 6, 2004

(65) Prior Publication Data

US 2005/0226378 A1    Oct. 13, 2005

(51) Int. Cl.
*H01J 35/32*    (2006.01)
*G21K 5/04*    (2006.01)
*A61N 5/10*    (2006.01)

(52) U.S. Cl. .............................. 378/119; 378/64; 378/65
(58) Field of Classification Search .................. 378/44, 378/64, 65, 119, 121, 122, 124, 140, 143; 600/2, 427
See application file for complete search history.

(56) References Cited

U.S. PATENT DOCUMENTS

| | | | | |
|---|---|---|---|---|
| 3,920,999 A | * | 11/1975 | Drexler et al. | 378/119 |
| 3,925,660 A | * | 12/1975 | Albert | 378/45 |
| 4,903,287 A | * | 2/1990 | Harding | 378/119 |
| 5,090,043 A | | 2/1992 | Parker et al. | 378/121 |
| 5,153,900 A | | 10/1992 | Nomikos et al. | 378/65 |
| 5,157,704 A | * | 10/1992 | Harding | 378/119 |
| RE34,421 E | | 10/1993 | Parker et al. | 378/121 |
| 5,369,679 A | | 11/1994 | Sliski et al. | 378/65 |
| 5,422,926 A | | 6/1995 | Smith et al. | 378/121 |
| 5,428,658 A | | 6/1995 | Oettinger et al. | 378/119 |
| 5,442,678 A | | 8/1995 | Dinsmore et al. | 378/137 |
| 5,452,720 A | | 9/1995 | Smith et al. | 600/427 |
| 5,528,652 A | | 6/1996 | Smith et al. | 378/65 |
| 5,566,221 A | | 10/1996 | Smith et al. | 378/145 |
| 5,621,780 A | | 4/1997 | Smith et al. | 378/65 |
| 5,729,583 A | * | 3/1998 | Tang et al. | 378/122 |
| 5,737,384 A | | 4/1998 | Fenn | 378/65 |

(Continued)

OTHER PUBLICATIONS

B. D. Cullity and S. R. Stock. Elements of X-Ray Diffraction, third edition (NJ: Prentice Hall, 2001), p. 11-19.*

*Primary Examiner*—Allen C. Ho
(74) *Attorney, Agent, or Firm*—Jenkins, Wilson, Taylor & Hunt, P.A.

(57) ABSTRACT

Devices and related methods are provided for irradiating a portion of a body. A device according to one embodiment can include a radiation needle, a fluorescent target, and an x-ray transmitting window. The radiation needle can include a radiation conduit having a first and second end for passing primary x-rays. An x-ray generator can generate the primary x-rays and pass the primary x-rays from the first end to second end. The fluorescent target can connect to the second end for absorbing the primary x-rays and produce by fluorescence secondary x-rays for irradiating a predetermined portion of the body. The fluorescent target having a surface for absorbing the primary x-rays to fluoresce and emit said secondary x-rays. The x-ray transmitting window can be positioned adjacent to the fluorescent target such that the secondary x-rays exit through the x-ray transmitting window. The secondary x-rays can irradiate target tissue within the body.

3 Claims, 9 Drawing Sheets

U.S. PATENT DOCUMENTS

| | | | |
|---|---|---|---|
| 5,816,999 A | 10/1998 | Bischoff et al. .............. 600/3 |
| 5,854,822 A | 12/1998 | Chornenky et al. ......... 378/122 |
| 5,940,469 A * | 8/1999 | Hell et al. .................. 378/143 |
| 6,001,054 A | 12/1999 | Regulla et al. ................ 600/1 |
| 6,069,938 A | 5/2000 | Chornenky et al. ......... 378/122 |
| 6,095,966 A | 8/2000 | Chornenky et al. ............ 600/3 |
| 6,108,402 A | 8/2000 | Chornenky ................ 378/119 |
| 6,141,400 A * | 10/2000 | Schardt et al. ............. 378/124 |
| 6,195,411 B1 | 2/2001 | Dinsmore ................... 378/65 |
| 6,245,047 B1 | 6/2001 | Feda et al. ................ 604/192 |
| 6,275,566 B1 | 8/2001 | Smith et al. ............... 378/122 |
| 6,285,735 B1 | 9/2001 | Sliski et al. ................. 378/65 |
| 6,289,079 B1 | 9/2001 | Chornenky et al. ......... 378/143 |
| 6,301,328 B1 | 10/2001 | Sliski et al. ................. 378/65 |
| 6,320,932 B2 | 11/2001 | Dinsmore ................... 378/65 |
| 6,377,846 B1 | 4/2002 | Chornenky et al. ........... 604/20 |
| 6,415,016 B1 | 7/2002 | Chornenky et al. ......... 378/122 |
| 6,421,416 B1 | 7/2002 | Sliski et al. ................. 378/65 |
| 6,473,491 B2 | 10/2002 | Chornenky et al. ......... 378/122 |
| 6,477,235 B2 | 11/2002 | Chornenky et al. ......... 378/147 |
| 6,480,567 B1 | 11/2002 | Feda et al. ................... 378/65 |
| 6,480,568 B1 | 11/2002 | Dinsmore ................... 378/65 |
| 6,480,573 B1 | 11/2002 | Dinsmore ................. 378/136 |
| 6,493,419 B1 | 12/2002 | Dinsmore ................... 378/65 |
| 6,496,561 B1 | 12/2002 | Meyer et al. ................ 378/65 |
| 6,546,077 B2 | 4/2003 | Chornenky et al. ......... 378/122 |
| 6,580,940 B2 | 6/2003 | Gutman .................... 600/427 |
| 7,120,224 B2 * | 10/2006 | Gutman ...................... 378/37 |
| 2004/0013230 A1 * | 1/2004 | Kumakhov ................. 378/65 |

* cited by examiner

DEVICES AND METHODS FOR TARGETING INTERIOR CANCERS WITH IONIZING RADIATION

TECHNICAL FIELD

The present invention relates to devices and methods for delivering therapeutic ionizing radiation to interior cancerous tissues. More particularly, the present invention relates to devices and methods for delivering therapeutic ionizing radiation in situ to targeted cancerous tissues without the deposition of radiation into intervening normal healthy tissues.

BACKGROUND ART

The importance of improving the treatment of cancerous tissue needs scarcely to be emphasized. Local cancerous tissue is typically treated with surgery and/or radiation therapy. Radiation therapy has been an important part of cancer treatment ever since malignant tumors were discovered to be susceptible to ionizing radiation.

A fundamental principal of radiation therapy is to deliver a therapeutic dose to the target tissue while minimizing the dose to surrounding healthy tissue, i.e., maximizing the therapeutic ratio. This is particularly challenging for deeply seated cancers since external therapy beams must traverse relatively large volumes of healthy tissue in order to reach the target. A variety of techniques have been developed to improve the therapeutic ratio for such external beam treatments, including three-dimensional (3-D) treatment planning, use of non-coplanar beams, stereotactic radiosurgery, intensity modulation, and charged particle therapy (e.g., protons). Radiation must be of a very high energy (short wavelength) in order to treat cancers that are deeply seated inside the body because this radiation must pass through overlying skin and sometimes other tissue, such as bone, which is more x-ray absorbent. Because such therapeutic radiation can be harmful to healthy tissue, the use of these techniques is limited to the dose amount that can be tolerated by the healthy tissues surrounding the target cancer.

Intraoperative radiation and brachytherapy are techniques developed to reduce the impact of radiation therapy to surrounding healthy tissues. During intraoperative therapy, adjacent healthy tissues are physically moved such that a radiation applicator can be applied directly to the target volume while applying a reduced amount of radiation to the adjacent healthy tissues. The radiation applicator can be an external photon beam generator, electron generator, or a radioactive material.

Brachytherapy involves implanting radioactive sources near or within cancerous tissue to provide interior radiation while minimizing exposure to surrounding healthy tissue. Brachytherapy has proven useful, but still carries the inherent risk of a radiation source that cannot be turned off. The handling, preparation, and use of such sources require that physicians, physicists, radiologists, and other personnel experience occupational exposure to ionizing radiation. Radioactive sources must be stored in shielded storage areas. Further, there are environmental and security issues regarding the disposal of these radioactive sources.

A number of devices have been developed for applying soft x-rays to interior cancer tissues in attempts to reduce radiation deposition in surrounding normal tissues. Some such devices generate soft x-rays inside the body using small x-ray generators inserted near or into cancer tissue. For example U.S. Pat. No. 5,153,900 to Nomikos et al. and U.S. Pat. No. 5,442,678 to Dinsmore et al. disclose a device consisting of a miniaturized low power x-ray source that generates electrons from an extracorporeal cathode, which emits these electrons down an evacuated tube towards an anode that is positioned inside the body. The x-ray radiation is then generated as these electrons impact the anode and is emitted approximately spherically. U.S. Pat. No. 5,369,679 to Sliski et al. and U.S. Pat. No. 5,422,926 Smith et al. disclose improvements to the x-ray generator. U.S. Pat. No. 5,452,720 to Smith et al. and U.S. Pat. No. 5,528,652 to Smith et al. disclose a method of using such a device that generates x-rays from an electron beam inside the body for the purpose of treating brain tumors.

A balloon shaped applicator system to attach to the end of the electron transmitting tube has been disclosed in U.S. Pat. No. 5,566,221 to Smith et al. and U.S. Pat. No. 5,621,780 to Smith et al. In this applicator system, a variable sized balloon is used to position the anode in the center of a body cavity, such as the bladder, to ensure a uniform dose is delivered to the entire inner surface of the cavity. An additional applicator system design is disclosed in U.S. Pat. Nos. 6,285,735, 6,301,328, and 6,421,416, each to Sliski et al. The additional applicator system expands upon the balloon applicator system to include cylindrical dose distributions and flat dose distributions through a surface external to the electron transmitting tube's anode. A biocompatible sheath for such an electron transmitting tube is disclosed in U.S. Pat. Nos. 6,245,047 and 6,480,567, each to Feta et al. The biocompatible sheath is composed of a polymer sheath that slips over the tube and creates a barrier between the body and the device. This allows the device to be reused in multiple patients by simply replacing the biocompatible sheath. These above devices have the difficulty that if the electron beam impacts the tube wall, then Bremsstrahlung radiation is emitted laterally into normal tissue. Another problem with placing an anode inside the body is that the anode will generate heat since only a small fraction of the energy from the electrons is converted to x-ray energy.

U.S. Pat. No. 5,737,384 to Fenn discloses a tube for insertion into the body similar to that described above in which electrons are transmitted from an extracorporeal cathode to an anode at the distal end of a tube inside the body. This device combines multiple tubes for the purpose of combining microwave energy with x-ray energy in the treatment volume. Radiofrequency treatment combined with x-ray or laser treatment is also suggested. However, this device does require that a large voltage be created inside the body in order to accelerate the electrons. There will also be significant heat generated at the anode when the x-rays are created at therapeutic intensities.

U.S. Pat. No. 5,428,658 to Oettinger et al. discloses a thermionic x-ray source mounted at the end of a flexible probe for insertion inside the body. This radiation device uses a laser beam to cause the emission of electrons at the device tip, where they are then accelerated over only a short distance before impacting an anode to produce x-ray radiation. Subsequent improvements to the thermionic flexible x-ray source are disclosed in U.S. Pat. Nos. 6,195,411, 6,320,932, 6,493,419, 6,480,568, and 6,480,573, each to Dinsmore. These devices require that a large voltage be created inside the body in order to accelerate the electrons after they have been stimulated at the cathode. There will also be significant heat generated at the anode when the x-rays are created at therapeutic intensities.

U.S. Pat. No. 5,090,043 to Parker et al. and U.S. Pat. Reexam No. 34,421 to Parker et al. disclose a miniature x-ray device for insertion inside the body with a glass enclosure. The device includes inserting a cathode and anode in a vacuum housing inside the body. U.S. Pat. Nos. 5,854,822, 6,069,938, 6,095,966, 6,108,402, 6,095,966, 6,289,079, 6,377,846, 6,415,016, 6,473,491, 6,477,235, and 6,546,077, each to Chornenky et al., disclose a similar miniature x-ray device for insertion inside the body and subsequent improvements to such a device. The miniature x-ray generator of the Chornenky Patents is powered by the insertion of a coaxial cable into the body to provide a potential for accelerating electrons from the cathode to the anode. Diamond is suggested for use in the anode and the housing. The device is suggested for use in treatment of Barrett's esophagus and in restenosis. This device still requires that a large voltage be created inside the body in order to accelerate the electrons. There is also significant heat generated at the anode when the x-rays are created at therapeutic intensities.

U.S. Pat. No. 6,275,566 to Smith et al. discloses a miniature x-ray device similar to those of the Chornenky Patents in which the entire x-ray generator, including the cathode and anode, are placed inside a miniature vacuum tube. The device is driven using an external voltage source similar to the miniature x-ray device disclosed in the Chornenky Patents, but it uses an alternating current rather than a direct current. The alternating current causes the anode and cathode to alternate with the same frequency as the current. With x-rays being generated at both electrodes, it is easier to cool each particular electrode because each electrode runs cooler than if either was the only point at which x-rays were generated. This device still requires that a large voltage be created inside the body in order to accelerate the electrons after they have been stimulated at the cathode. There is also significant heat generated at the anode when the x-rays are created at therapeutic intensities.

U.S. Pat. No. 6,001,054 to Regulla et al. discloses a device for increasing the local dose of ionizing radiation by introducing a metal surface near a tumor for the purpose of increasing local backscatter. The metal surface would be near the tumor and have a shape roughly conforming to the tumor. Ionizing radiation would be introduced from outside the body using standard external beam techniques. At the site of the tumor, the implanted metal surface creates backscatter radiation in the area of the tumor that increases local dose rates near the tumor between 2–200 times. The disclosure states that radiation from 40–400 keV will see the greatest increases in local dose rates, and suggests using metal surfaces with atomic numbers of approximately 20–40. The device is an improvement over standard external beam therapies, but still deposits a significant amount of radiation between the skin where the external beam enters the body and the tumor. Due to the fact that radiation between 40–400 keV is highly absorbed, significant irradiation of normal tissue between the skin and the tumor is expected.

U.S. Pat. No. 5,816,999 to Bischoff et al. discloses a device that delivers soft x-rays to target cancers via a flexible radiation transmitting catheter. This device transmits the soft x-rays generated outside the body directly to the site of an interior cancer. The soft x-rays are transmitted along a curved path through flexible hollow glass fibers by means of multiple surface specular reflections. Such a system involves a substantial reduction in beam intensity due to the multiple reflections required to transmit x-rays through a curved path and due also to the small transmission area of the capillaries relative to the total cross-sectional area of the radiation needle. The critical angle for total external reflection decreases as the energy of the x-ray photons increases. Consequently, a flexible x-ray transmitting radiation needle is limited to ultra soft x-rays with a cancer penetration depth on the order of millimeters and furthermore the large loss in radiation intensity caused by the reflections may increase the exposure time beyond clinically acceptable limits. This device may be useful for the treatment of surface lesions, but is not very useful for the treatment of larger neoplasms.

U.S. Pat. No. 5,816,999 to Bischoff et al. also discloses a dispersive distal cap. The cap absorbs parallel radiation from the flexible hollow glass fibers, and transmits it in a shaped pattern using fluorescence. The distal dispersive cap requires that primary x-rays and secondary, fluorescent x-rays must both be transmitted through the distal dispersive cap. This can lead to massive absorption losses, especially for the low energy (less than 20 keV) radiation transmitted by curved flexible hollow glass fibers using multiple specular reflections.

In view of the known devices for treating interior cancers, it is desirable to have an improved device for targeting interior cancerous tissues with ionizing radiation from an extracorporeal source. It is also desirable to have a radiation therapy device that minimizes the exposure of surrounding normal tissue to radiation. Further, it is desired to provide a radiation therapy device that applies a minimal amount of heat and voltage to the body during radiation therapy. A device that can deliver therapeutic radiation precisely to targeted tissues could have significant uses in a wide variety of therapeutic radiation oncology applications.

SUMMARY

Embodiments of a device and method are disclosed herein for irradiating a portion of a body. The device can include a rigid hollow radiation needle. The rigid hollow radiation needle can include at least one rigid radiation conduit having a first end and a second end. The rigid radiation conduit can be operable to pass primary x-rays from said first end to said second end. An x-ray generator can generate the primary x-rays. The x-ray generator can be operably connected to the first end to pass the primary x-rays to the second end by means of the rigid radiation conduit. The rigid radiation conduit in the rigid hollow radiation needle can have an internal diameter between one centimeter and 0.1 millimeters. The rigid hollow radiation needle can have a length between 2 centimeters and 75 centimeters. The device can also include a fluorescent target connected to the second end of the rigid radiation conduit and positioned to absorb the primary x-rays passed to the second end to produce, by fluorescence, secondary x-rays for irradiating a predetermined portion of the body. The fluorescent target can consist essentially of at least one element whose atomic number is between atomic number 11 and atomic number 83. The fluorescent target can have a shape with a surface for absorbing a fraction of the primary x-rays whereby the fluorescent target is caused to fluoresce and to emit the secondary x-rays. The secondary x-rays and primary x-rays can be related by a peak energy index ratio between 0.01 and 1. The device can also include an x-ray transmitting window positioned adjacent to the fluorescent target. The secondary x-rays can exit the rigid hollow radiation needle through the x-ray transmitting window and irradiate a volume conforming to a predetermined portion of a target tissue within the body. The volume can be between one tenth of a cubic millimeter and 115 cubic centimeters whereby the tissue is therapeutically irradiated by the secondary x-rays.

Other embodiments of devices and methods are disclosed herein for irradiating a portion of a body. The device can include a radiation needle having at least one radiation conduit having a first end and a second end. The radiation conduit can be operable to pass primary x-rays from said first end to said second end. The primary x-rays can be generated by an x-ray generator that is external to the body. The x-ray generator can be operably connected to the first end to pass the primary x-rays to the second end by means of the radiation conduit. The device can include a fluorescent target connected to the second end of the radiation conduit and positioned to absorb the primary x-rays passed to the second end to produce by fluorescence secondary x-rays for irradiating a predetermined portion of the body. The fluorescent target can have a shape with a surface for absorbing the primary x-rays whereby the fluorescent target is caused to fluoresce and to emit the secondary x-rays. The device can include an x-ray transmitting window positioned adjacent to the fluorescent target. The secondary x-rays can exit radiation needle through the x-ray transmitting window and irradiate a volume conforming to a predetermined portion of a target tissue within the body.

Some of the objects of the invention having been stated hereinabove, and which are addressed in whole or in part by the present invention, other objects will become evident as the description proceeds when taken in connection with the accompanying drawings as best described hereinbelow.

BRIEF DESCRIPTION OF THE DRAWINGS

Exemplary embodiments of the subject matter will now be explained with reference to the accompanying drawings, of which.

DETAILED DESCRIPTION OF THE INVENTION

Radiation delivery devices and methods enabling the precise delivery of ionizing radiation to designated target tissues, such as interior cancers, are described herein. These radiation devices and related methods also facilitate delivering therapeutic radiation with minimal radiation, heat deposition, and voltage into adjacent normal tissue. These devices and methods are described with regard to the accompanying drawings. It should be appreciated that the drawings do not constitute limitations on the scope of the disclosed devices and methods.

Radiation delivery devices as described herein are capable of delivering x-ray radiation for treating interior tissues. These radiation delivery devices can deliver x-ray radiation directly to a cancer site without significant energy deposition in normal tissue surrounding the cancer site. The volume through which the radiation is deposited can be selected to deliver therapeutic dosages precisely to a cancerous tumor or for other treatments requiring local ionizing radiation inside the body. The radiation delivery system can be used during a surgical or laparoscopic procedure to deliver a highly directed dosage of radiation to a tumor. Additionally, the radiation dosage can be directed and shaped for protecting areas of the body that are sensitive to radiation damage, such as the spinal cord.

A large number of neoplasms can be treated with the radiation delivery devices described herein. For example, the radiation delivery device can be used to treat intracranial metastases. Small intracranial metastases, such as brain tumors, can be detected via computed tomography (CT) or magnetic resonance imaging (MRI). In such a case, the position and dimensions of the metastatic tumor can be known with reasonable accuracy for treatment by the radiation delivery system.

Figure 1:
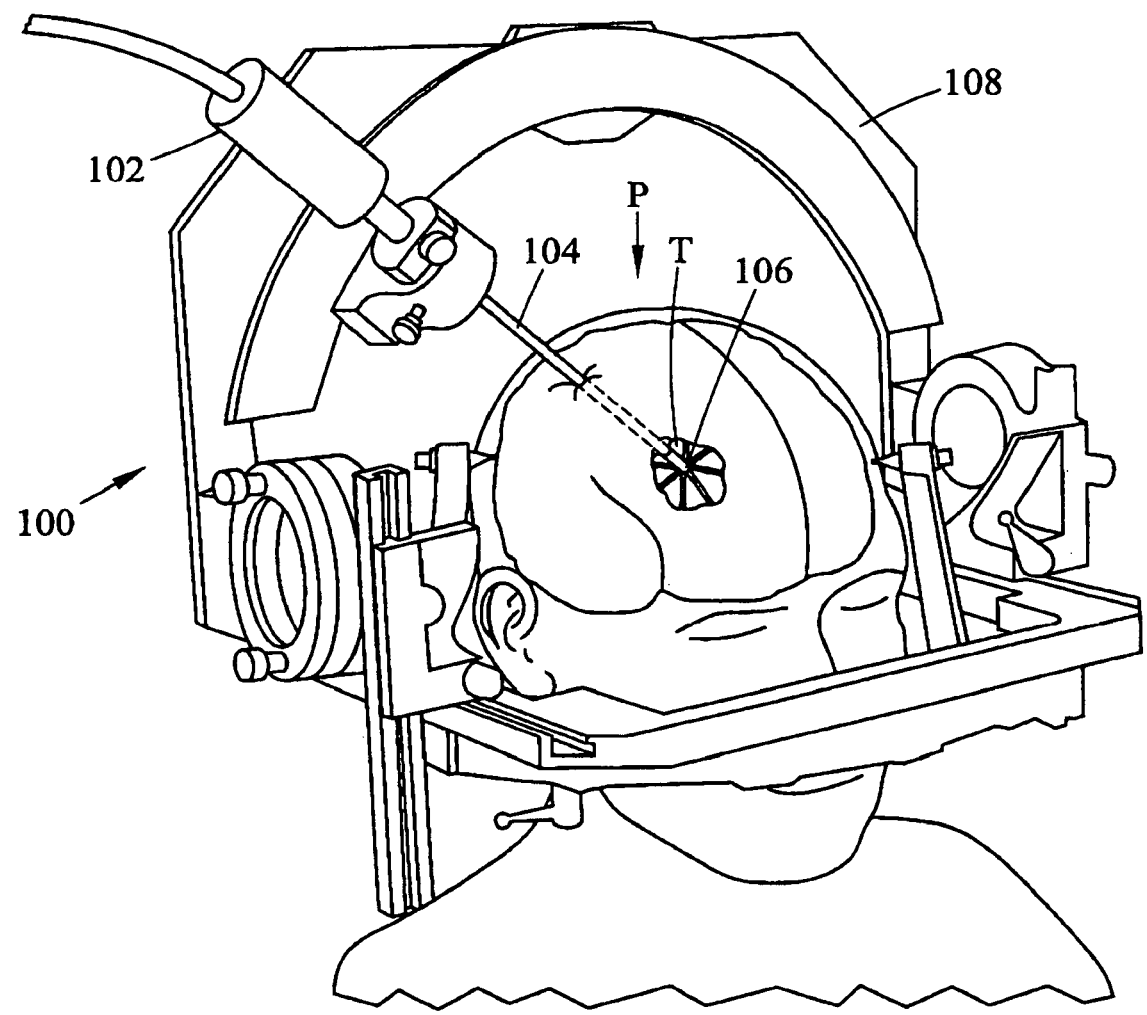
FIG. 1 is a perspective view of a patient with a brain tumor receiving radiation treatment from a radiation delivery system as described herein.

FIG. 1 illustrates a perspective view of a patient, generally designated P, with a brain tumor T receiving radiation treatment from a radiation delivery system, generally designated 100. Radiation delivery system 100 can comprise an x-ray generator 102, a radiation needle 104, a dispersion assembly 106, and a stereotactic frame 108. Stereotactic frame 108 can support and position x-ray generator 102, radiation needle 104, and dispersion assembly 106 with respect to patient P and tumor T. Stereotactic frame 108 can enable tumor T to be precisely targeted by radiation needle 104. According to one embodiment, the tumor location information can be provided by a MRI system or via CT. According to one embodiment, x-ray generator 102, radiation needle 104, and dispersion assembly 106 can be moved into position with respect to patient P and tumor T with computer-controlled robotic equipment (not shown).

Prior to applying radiation delivery system 100 to patient P, the position of tumor T can be determined via a suitable CT or MRI procedure known to those skilled in the art. Radiation needle 104 and dispersion assembly 106 can then be placed in a desired position inside or adjacent tumor T via a suitable surgical technique known to those of skill in the art. When dispersion assembly 106 is positioned, x-ray generator 102 can be energized to generate a beam of x-rays. The x-rays generated by x-ray generator 102 can then be directed through radiation needle 104 to dispersion assembly 106. Dispersion assembly 106 can receive the x-rays from radiation needle 104 and emanate the fluorescent x-rays in particular directions for precisely targeting tumor T without significant irradiation of surrounding healthy tissue.

In addition to application to brain tumors, radiation delivery system 100 can be applied to other tumors located in a patient. For example, radiation delivery system 100 can also be applied in a minimally invasive manner for treating cancer of the tongue or mouth. Non-spherical lesions can be treated by moving dispersion assembly 106 to different positions relative to the tumor or by utilizing a dispersion tip that produces a desired, non-symmetric radiation field geometry for fitting the tumor. Further, radiation delivery system 100 can also be used as an intraoperative radiation source for focal irradiation of the surgical cavity in some situations (e.g., intraoperative treatment of soft tissue sarcomas and pelvic tumors).

X-Ray Generator

Figure 2:
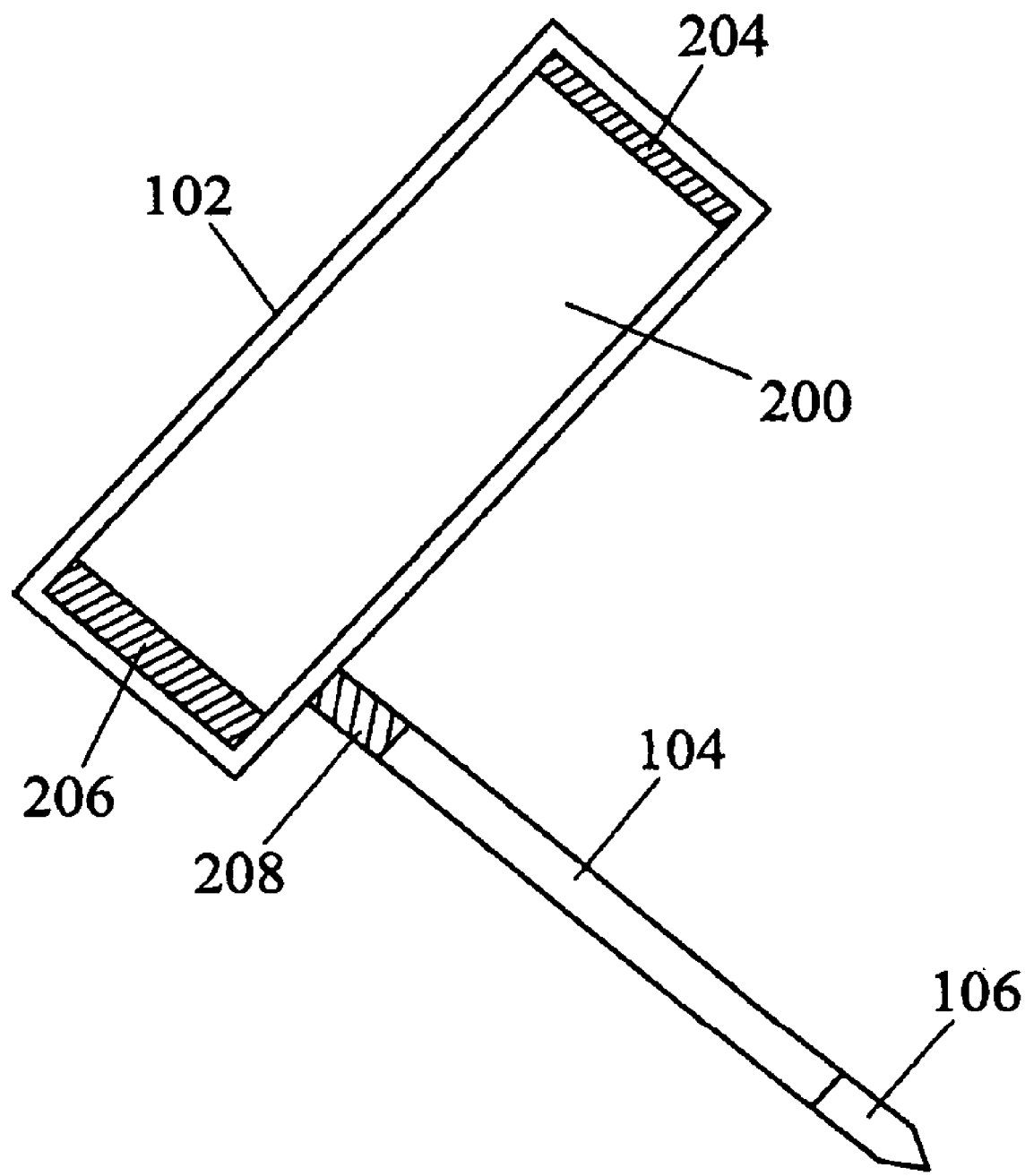
FIG. 2 is a cross-section view of an x-ray generator with a radiation needle and a dispersion assembly.

FIG. 2 illustrates a cross-section view of one embodiment of x-ray generator 102 with radiation needle 104 and dispersion assembly 106. In this embodiment, x-ray generator 102 can utilize a potential between 1–100 keV to accelerate electrons through a vacuum 200 from a cathode 204 to an anode 206. When anode 206 absorbs the accelerated electrons, x-ray radiation can be generated having different energy spectrums depending on the material of anode 206 as well as the voltage through which the electrons were accelerated. The generated x-ray can have radiation energy between about 1 and 100 keV.

X-ray generator 102 can also include a collimating or focusing optic 208 positioned between vacuum 200 and radiation needle 104 and suitable for collimating or focusing the x-ray radiation generated by x-ray generator 102. Focusing optic 208 can collimate or focus the x-rays for passage through the interior of radiation needle 104 to dispersion assembly 106.

According to one embodiment, x-ray generator 102 can comprise a collimated x-ray generation unit and optic 208 in combination such as the MICRO MAX® System and a rotating anode generator (RAG) (available from Osmic, Inc. of Auburn Hill, Mich., U.S.A.). Table 1 shown below summarizes the performance of selected products available from Osmic, Inc.

TABLE 1

Performance Summary of Selected Parallel Beam Systems

| X-Ray Generator | RAG 0.2 mm | RAG 0.07 mm | Micro Max ® |
|---|---|---|---|
| Spot Size | 0.2 × 0.2 mm | 0.07 × 0.07 mm | 0.02 × 0.02 mm |
| Power | 3.0 kW | 800 W | 30 W |
| Optic | Parabolic CMF | Parabolic CMF | Parabolic CMF |
| Coating | W based | W based | W based |
| Beam Size | 1.7 × 1.7 mm | 1.7 × 1.7 mm | 1.8 × 1.8 mm |
| Divergence (FWHM) | 0.03 degrees | 0.027 degrees | 0.020 degrees |
| Divergence (FW10%) | 0.1 degrees | 0.055 degrees | 0.044 degrees |
| Flux (photons/second) | $1.5 \times 10^9$ | $1.1 \times 10^9$ | $2.1 \times 10^8$ |

As demonstrated by Table 1 above, the collimation that can produced by multilayer collimating optics in a parallel beam system is so high that the spread of the beam along a six inch path at full width half maximum (FWHM) is less than 0.08 mm. Therefore, such a beam can be passed through a radiation needle (such as radiation needle 104 shown in FIGS. 1 and 2) having an interior diameter of 1 mm with minimal losses through absorption of x-rays in the radiation needle walls. In the best case, a divergence of 0.02 degrees (FWHM) expands to only 0.05 mm over this distance. For the full width 10% worst case of 0.1 degrees, the spread of the beam is 0.26 mm, and in the best case of 0.44 degrees is 0.12 mm.

As the x-rays pass through focusing optic 208 into radiation needle 104, the x-rays can be substantially collimated and parallel with radiation needle 104. The x-rays generated by x-ray generator 102 can travel through radiation needle 104 and contact a fluorescent target (not shown in FIG. 2) contained in dispersion assembly 106. The fluorescent target can absorb the x-rays from x-ray generator 102 and fluoresce with these x-rays.

The x-ray beams generated by x-ray generator 102 for transmission to dispersion assembly 106 are referred to herein as primary x-rays. The x-rays that fluoresce, or emanate, from the fluorescent target in dispersion assembly 106 are referred to herein as secondary x-rays. The energy of the secondary x-rays is lower than the energy of the primary x-rays. The peak energy index ratio is defined as the ratio of the peak intensity energy of the secondary x-rays to the peak energy of the primary x-rays in keV. The energy of the secondary x-rays of the fluorescent target can be selected by the fluorescent target material and the primary x-ray energy generated by x-rays generator 102.

The highest energy primary x-ray, the short-wavelength limit x-rays, can be approximately 100 keV for a 100 kV acceleration potential. The lowest energy secondary x-rays can be approximately 1.04 keV, the Kα energy of Na. For such a combination, the lower limit of the peak energy index ratio can be 0.0104. The upper limit to the range of peak energy index ratios is the largest ratio between the ratio of the Kα peak energy to the K absorption edge for a particular element. This ratio is largest, over the range of elements considered herein (atomic numbers 11–83), for the element Na, atomic number 11. For Na, the ratio of the Kα peak energy to the K absorption edge is 0.971. Therefore, according to one embodiment, the range of peak energy index ratios useful for x-ray generator 102 is 0.0104 to 0.971.

According to one embodiment, the spectrum of the primary x-rays generated by x-ray generator 102 is a function of voltage applied between cathode 204 and anode 206, the electron current, and the composition of anode 206. X-ray generator 102 can include an external power supply for generating a voltage between cathode 204 and anode 206 of approximately 10–100 kilovolts (kV). A current can be generated between approximately 10 and 100 milliamps (mA). Alternatively, the current can be as low as 10 nanoamps (nA) or lower in some miniature x-ray generators.

Anode 206 can comprise copper (Cu), titanium (Ti), molybdenum (Mo), tungsten (W), chromium (Cr), cobalt (Co) or another suitable material known to those of skill in the art. The peak energies are due to electrons absorbing energy and moving to a higher orbit, then releasing that energy in the form of x-ray photons as they move back down to their equilibrium shells. In addition to characteristic radiation, Bremsstrahlung radiation is a background base level of radiation that is created from 0 keV to the excitation voltage of the x-ray tube.

Figure 3:
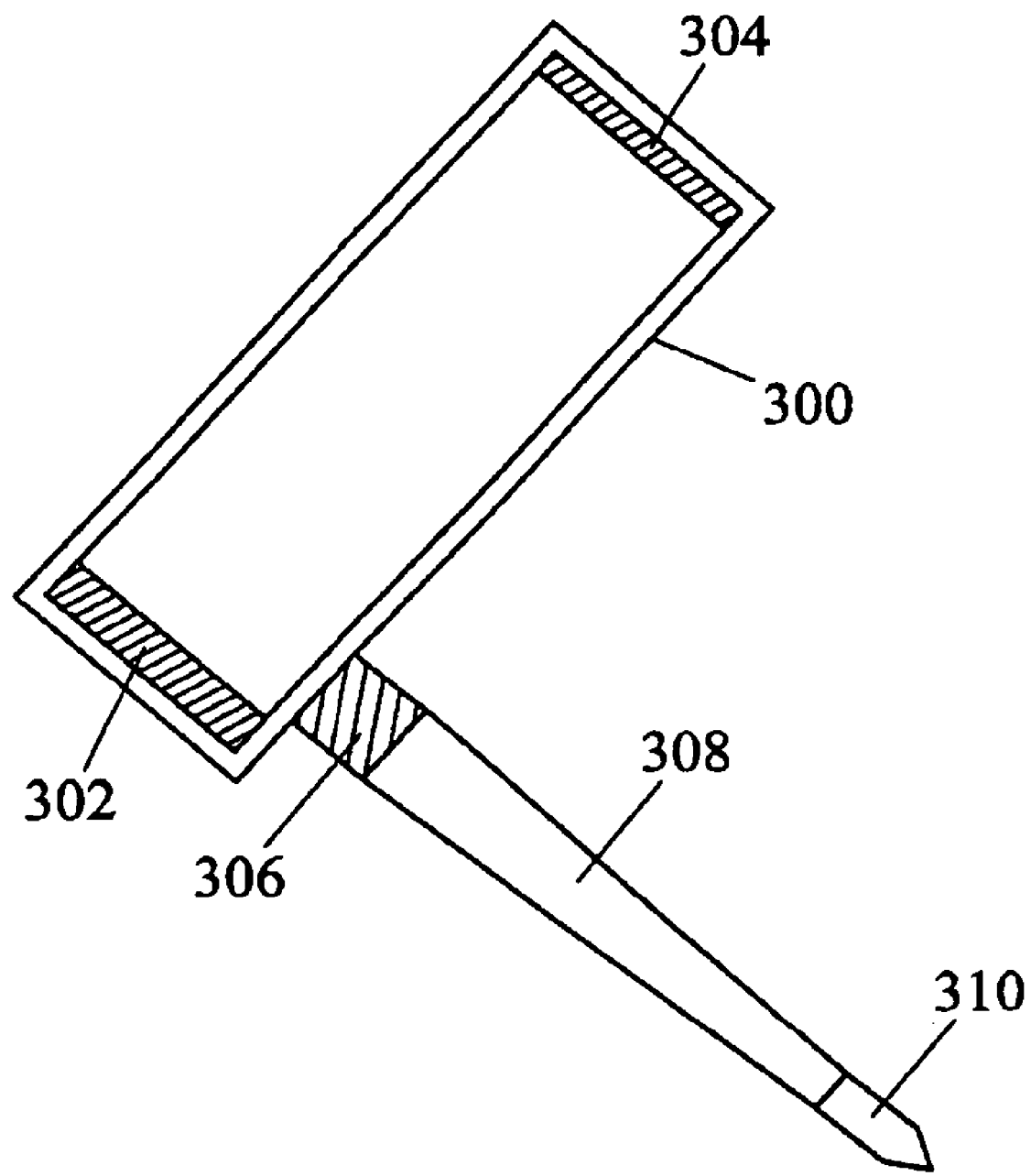
FIG. 3 is a cross-section view of another embodiment of an x-ray generator, focusing optic, radiation needle, and dispersion assembly.

FIG. 3 illustrates a cross-section view of another embodiment of an x-ray generator 300, anode 302, cathode 304, focusing optic 306, radiation needle 308, and dispersion assembly 310. In this embodiment, radiation needle 308 is a tapered cylinder rather than a straight cylinder. In such a case, the diameter would decrease from x-ray generator 300 to dispersion assembly 310. This particular embodiment can be used with focusing optic 306 to focus x-rays on dispersion assembly 310.

Radiation Needle

Figure 4:
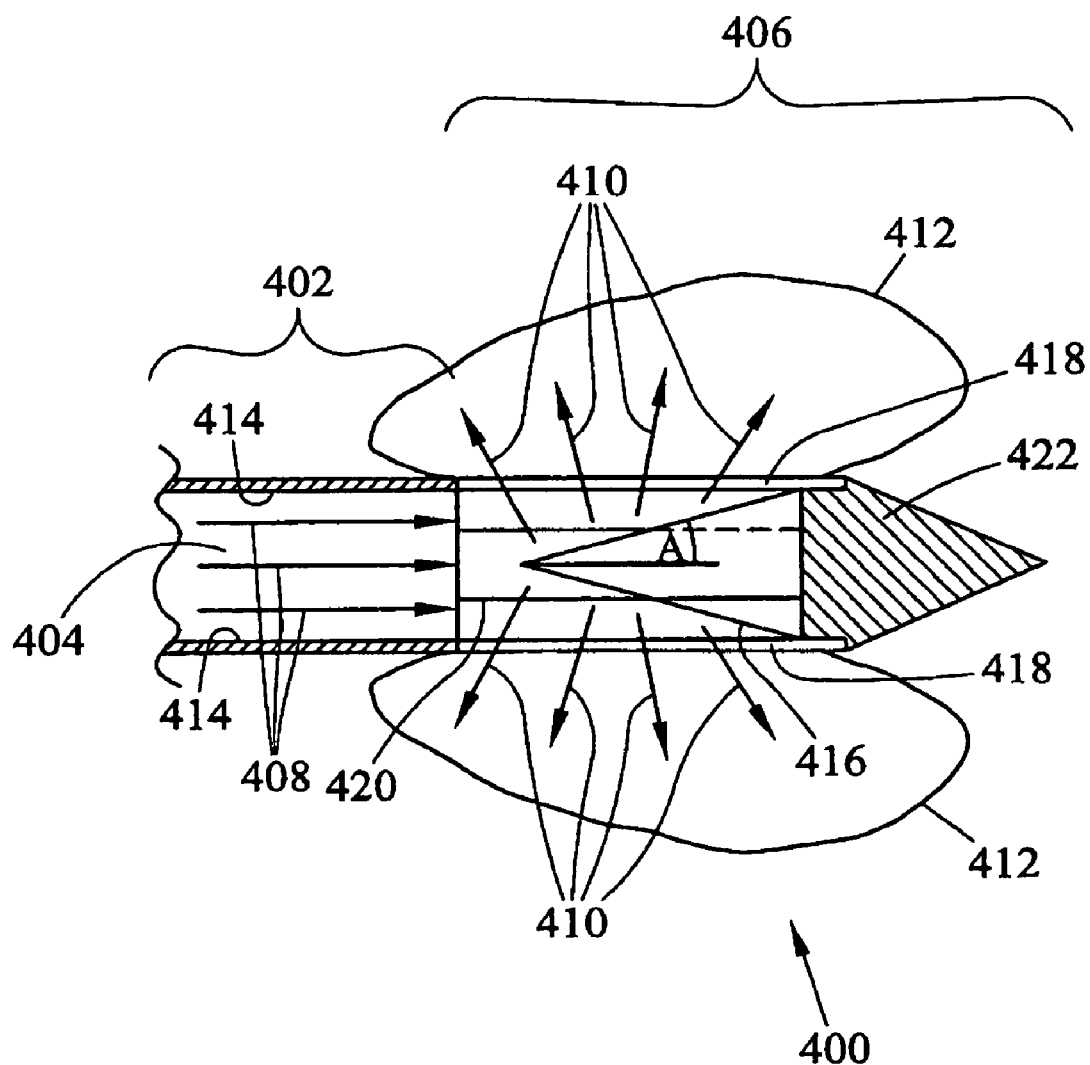
FIG. 4 is a cross-section view of an exemplary embodiment of a radiation needle device and an attached dispersion assembly.

FIGS. 4–7 illustrate cross-section views of different exemplary embodiments of a radiation needle device and attached dispersion assembly for use in radiation delivery system 100. Referring to FIG. 4, a radiation needle, generally designated 400, can include a radiation conduit 402 having a substantially straight, hollow interior 404 extending from an x-ray generator (such as x-ray generator 102 shown in FIGS. 1 and 2 and not shown) to a dispersion assembly, generally designated 406. Primary x-rays 408

(represented by direction arrows) can be transmitted from the x-ray generator through interior 404 to dispersion assembly 406. Dispersion assembly 406 can include components for fluorescing primary x-rays 408 as secondary x-rays 410 (represented by direction arrows) in desired directions for irradiating nearby neoplasms. Secondary x-rays 410 can irradiate a volume of tissue shaped approximately as treatment volume 412. Radiation needle 400 can have an outside diameter of approximately 1 millimeter or greater. Hollow interior 404 can be cylindrically-shaped with a diameter of between about 0.01 and 10 millimeters.

Primary x-rays 408 are aligned for travel through interior 404 of radiation needle 400. Primary x-rays may contact interior surface 414 of radiation needle 400. Radiation conduit 402 can be made of a material of high atomic number and sufficiently thick to absorb any primary x-rays 408 incident on a surface 414 of radiation needle 400 for preventing the release of primary x-rays 408 into undesired areas of the body, such as into surrounding normal healthy tissue.

In order to determine the thickness of shielding required in radiation needle 400, the absorption of x-rays in the shielding material must be calculated. The linear absorption coefficient $\mu$ (cm$^1$) of each layer of radiation needle 400 can be calculated. For a material composed of multiple elements, the overall mass absorption coefficient can be calculated using the following equation (where the values of mass absorption coefficients $(\mu/\rho)_n$ for each element at various incident energies can be obtained from standard sources):

$$\frac{\mu}{\rho_0} = \sum_n \left(\frac{\mu}{\rho}\right)_n$$

In this equation, $\mu$, $_{92\ o}$, and $\rho_n$ represent the linear absorption coefficient, the density of the material, and the density $\rho_n$, (g/cm$^3$) of each element n as it is found in the material through which the x-rays pass.

Using the linear absorption coefficient, the fraction of photons having a specific energy and penetrating a specific distance (x) can be determined from the following equation:

$$\frac{i}{i_0} = e^{-\mu x}$$

The above equation calculates the intensity ratio of the intensity (i) of photons of a given energy that have penetrated a given material a distance (x) divided by the initial intensity ($i_o$). Using the above equation, the thicknesses (in millimeters) of a radiation needle 400 required to absorb 99% of primary x-rays 408 of various energies when composed of various pure elements are shown in Table 2 below.

TABLE 2

Linear absorption in millimeters required to absorb 99% of various low x-ray energies in selected elements

| Energy (keV) | Iron (Z = 26) | Silver (Z = 47) | Gold (Z = 79) | Lead (Z = 82) |
|---|---|---|---|---|
| 4.51 | 0.003 | 0.0042 | 0.0027 | 0.004 |
| 8.04 | 0.019 | 0.02 | 0.012 | 0.018 |
| 17.48 | 0.139 | 0.15 | 0.02 | 0.035 |
| 25.27 | 0.35 | 0.15 | 0.045 | 0.07 |

TABLE 2-continued

Linear absorption in millimeters required to absorb 99% of various low x-ray energies in selected elements

| Energy (keV) | Iron (Z = 26) | Silver (Z = 47) | Gold (Z = 79) | Lead (Z = 82) |
|---|---|---|---|---|
| 32.19 | 0.8 | 0.14 | 0.1 | 0.15 |
| 57.52 | 4.05 | 0.65 | 0.45 | 0.7 |
| 70 | 6.5 | 1.05 | 0.7 | 1.1 |
| 80 | 10 | 1.65 | 1.1 | 1.7 |

Radiation needle 400 can be composed of any suitable shielding material known to those of skill in the art for absorbing at least 99% of primary x-rays 408 incident upon it including lead, silver, gold, tantalum, tungsten, platinum, nickel, iron, chromium, and combinations thereof. Table 2 provides estimates for the thickness of radiation needle 400 required to shield the body from primary x-rays 408. In another embodiment, radiation needle 400 can be composed of two or more layers. In such a case, the inner layer is preferably composed of a material often used in needles such as stainless steel, and the outer, thinner layer is preferably composed of a heavier, shielding element as suggested in Table 2.

Interior 404 can contain air or another suitable material known to those of skill in art for allowing primary x-rays 408 to pass from the x-ray generator to dispersion assembly 406. Interior 404 can also be evacuated for passing primary x-rays 408 and especially primary x-rays having lower (softer) energy, which have significant loss in air.

Dispersion Assembly

Dispersion assembly 406, as shown in FIG. 4, can include a fluorescent target 416, an x-ray transparent window 418, a support 420, and a penetration tip 422. Primary x-rays 408 can travel through radiation needle 402 and strike an angled surface of fluorescent target 416. Primary x-rays 408 can be absorbed by target 416 and target 416 can fluoresce, or emanate, secondary x-rays 410 in specific directions based on the shape and position of the surface of target 416. The direction and penetration depth of secondary x-rays 410 can be known for properly positioning dispersion assembly 406 with respect to a tumor such that the majority of radiation is deposited within the tumor and minimizes irradiation of normal tissue.

Target 416 can be made of different materials for affecting the energy, and therefore tissue penetration, of secondary x-rays 410. Fluorescent target 416 can be made of any element between atomic number 11 and 83 or combinations thereof. The higher the atomic number of the target material, the higher the energy and the deeper the penetration depth of secondary x-rays 410. The deeper the penetration depth of secondary x-rays 410, the larger the treatment volume. Also, the closer the energy of secondary x-rays 410 to the energy of primary x-rays 408, the higher the peak energy index ratio. The peak energy index ratio is always less than 1, but the closer it is to 1, the less energy is lost in the conversion from primary x-rays 408 to secondary x-rays 410.

Figure 5:
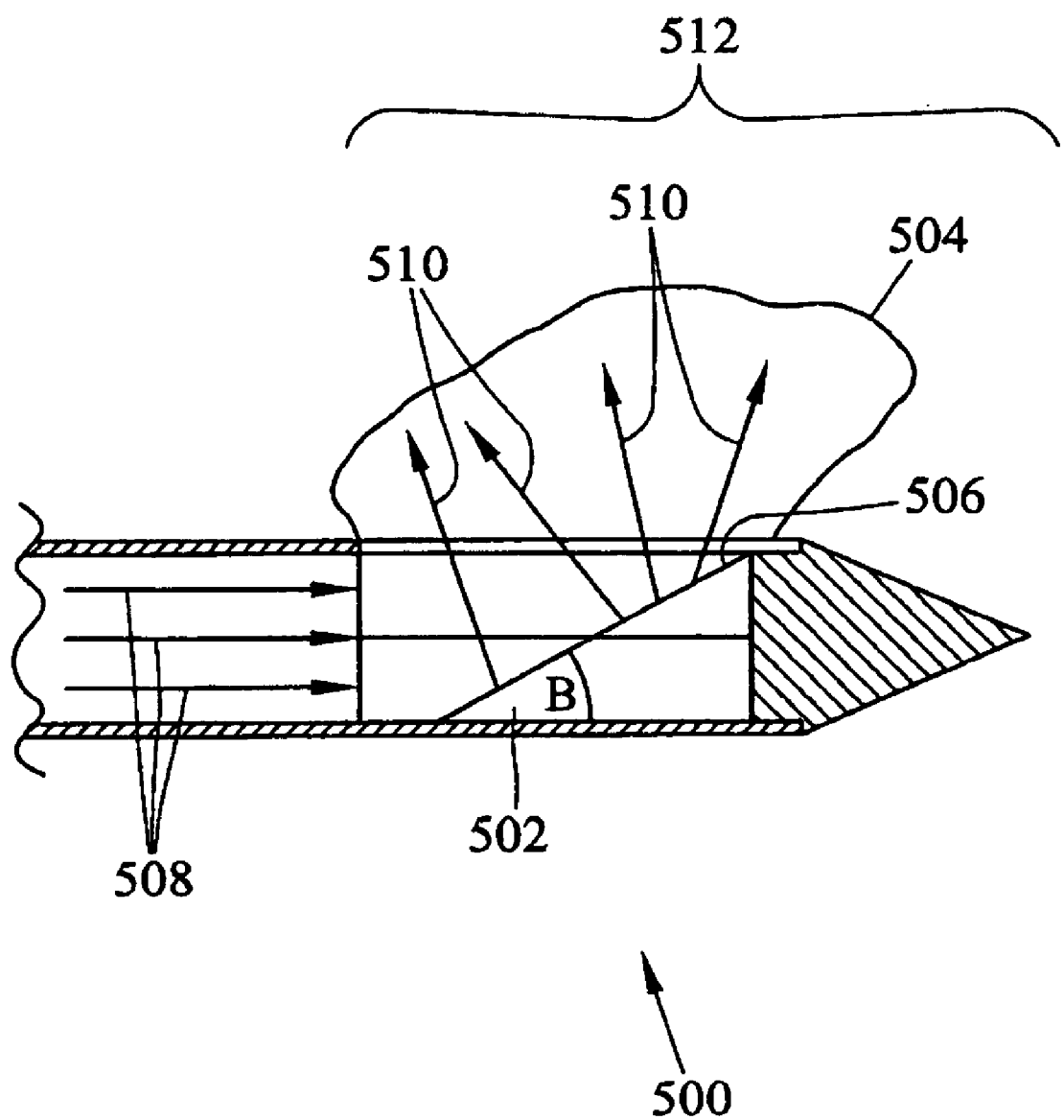
FIG. 5 is a cross-section view of another exemplary embodiment of a radiation needle device and an attached dispersion assembly.
Figure 6:
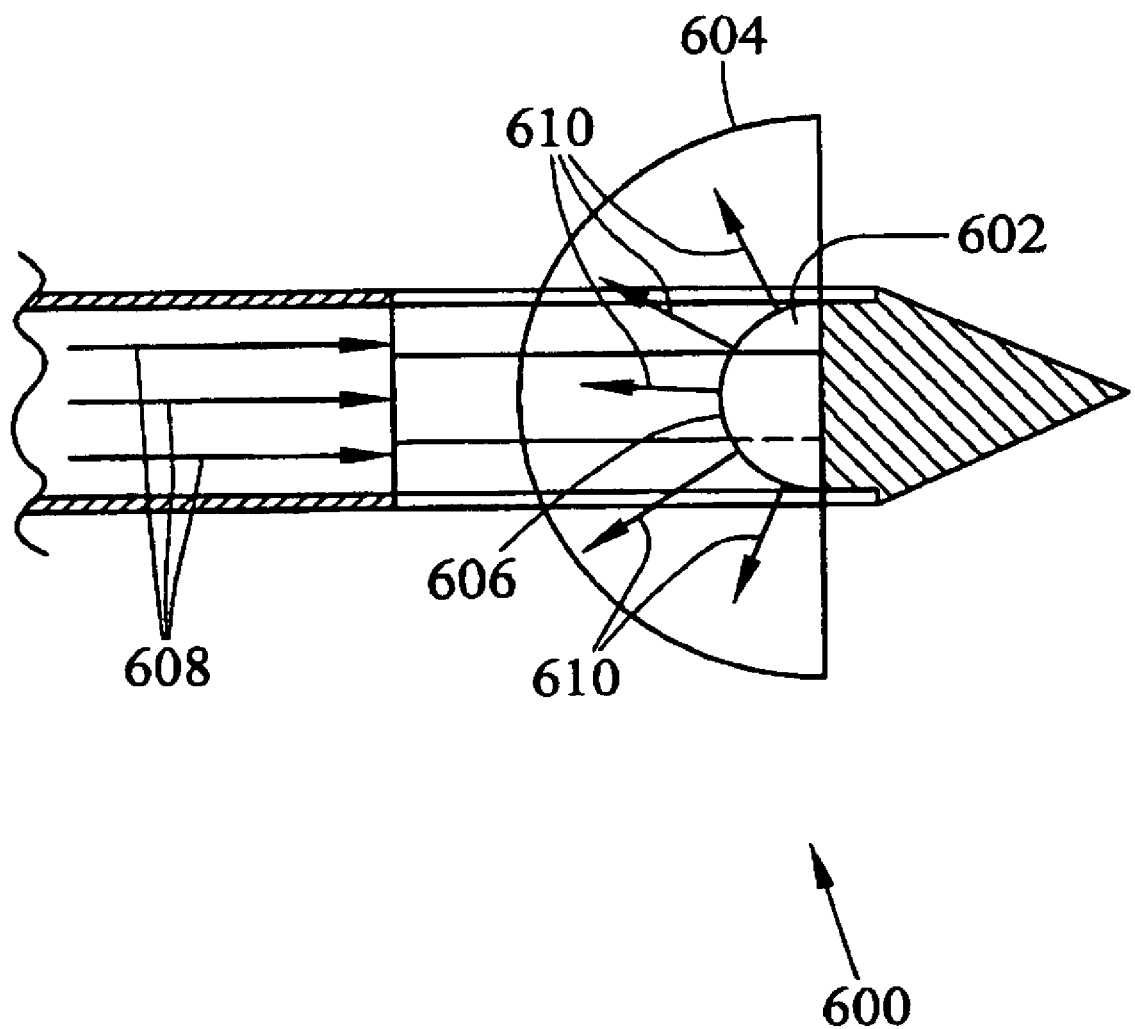
FIG. 6 is a cross-section view of another exemplary embodiment of a radiation needle device and an attached dispersion assembly.

The path of secondary x-rays 410, and subsequently treatment volume 412, can be directed based on the shape of target 416. Secondary x-rays 410 are created by fluorescing target 416. X-rays created via fluorescence, such as secondary x-rays 410, can spread in all directions from fluorescent target 416 in a generally spherical pattern, but changing the shape of fluorescent target 416 can alter the shape of treatment volume 412. Therefore, fluorescent target 416 can have different shapes. These shapes include, but are not limited to, a conical target as shown in FIG. 4, a planar target as shown in FIG. 5, a curved target as shown in FIG. 6, or a combination of such shapes. Changing the shape of fluorescent target 416 can allow irradiation volume 412 to match the shape of a tumor as closely as possible. It is important to note that fluorescent target 416 can shield both primary x-rays 408 and secondary x-rays 410 from exiting through penetration tip 422. According to one embodiment, target 416 can be sufficiently thin to pass primary x-rays 408 into the body to contribute to irradiation volume 412.

In the embodiment shown in FIG. 4, target 416 has a conically-shaped surface with its pointed end directed towards primary x-rays 408. The shape and position of the surface of target 416 with respect to primary x-rays 408 causes secondary x-rays 410 to emanate in a generally lateral direction with respect to the path of primary x-rays 408. Secondary x-rays 410 can irradiate a volume 412 of tissue. Angle A determines the sharpness of conically-shaped fluorescent target 416. As angle A decreases, conically-shaped fluorescent target 416 becomes sharper and longer, and treatment volume 412 lengthens along the axis of radiation needle 400. As treatment volume 412 lengthens, the dose rate can decrease as the same intensity of primary x-rays 408 is transmitted to a larger treatment volume. Angle A can be between about 0 and 90 degrees.

Secondary x-rays 410 can be directed based on the position of x-ray shielding positioned on window 418. The x-ray shielding can block or filter portions of secondary x-rays 410. Such x-ray shields can be made of the same materials used to shield radiation conduit 402 to prevent unwanted lateral dispersion of primary x-rays 408 as described above in Table 2. Window 418 of dispersion assembly 406 can be essentially transparent for allowing secondary x-rays 410 to pass unimpeded into the body. Window 418 can also seal target 416 to prevent leakage of body fluids into radiation needle 400. Window 418 can be made of beryllium, low average atomic number polymers including polycarbonates, or other suitable transparent materials known to those of skill in the art. The material of window 418 can have the lowest possible absorption of x-rays such that the most possible secondary x-rays 410 may pass from fluorescent target 416 to treatment volume 412.

Support 420 can extend from radiation conduit 402 to fluorescent target 416 in order to hold target 416 in position with respect to radiation conduit 402. In one embodiment, support 420 is part of radiation needle 400. In such an embodiment, window 418 is cut out of radiation conduit 402. Support 420 can comprise a rigid material to maintain the structure and position of dispersion assembly 406, fluorescent target 416, x-ray transparent window 418, and penetration tip 422 with respect to each other when inserted into a body.

FIG. 5 shows a radiation needle, generally designated 500, having a fluorescent target 502 according to one embodiment. Fluorescent target 502 can have a different shape than fluorescent target 416 (FIG. 4). As a result, fluorescent target 502 can irradiate a different treatment volume 504 than target 416. Target 502 can have a planar surface 506 angled with respect to the path of primary x-rays 508 for directing secondary x-rays 510 substantially to one side of dispersion assembly 512. In this embodiment, surface 506 is substantially planar and angled with an angle B with respect to the axis of radiation needle 500. Fluorescent target 502 can irradiate a treatment volume 504 such that secondary x-rays 510 emanate towards one side of radiation needle 500. As angle B decreases, planar fluorescent target 502 becomes longer, and treatment volume 504 lengthens along the axis of radiation needle 500. As irradiation volume 504 lengthens, the dose rate can decrease as the same intensity of primary x-rays 508 is transmitted to a larger volume of tissue. In this embodiment, angle B can be between about 0 and 90 degrees.

FIG. 6 shows a radiation needle, generally designated 600, having a fluorescent target 602 according to another embodiment. Fluorescent target 602 can have a different shape than fluorescent target 416 (FIG. 4). As a result, fluorescent target 602 can irradiate a different treatment volume 604 than target 416. Target 602 can have a convex surface 606 with respect to the path of primary x-rays 608. Convex fluorescent target 602 can direct secondary x-rays 610 to irradiate a nearly hemispherical volume of tissue as shown by treatment volume 604.

Figure 7:
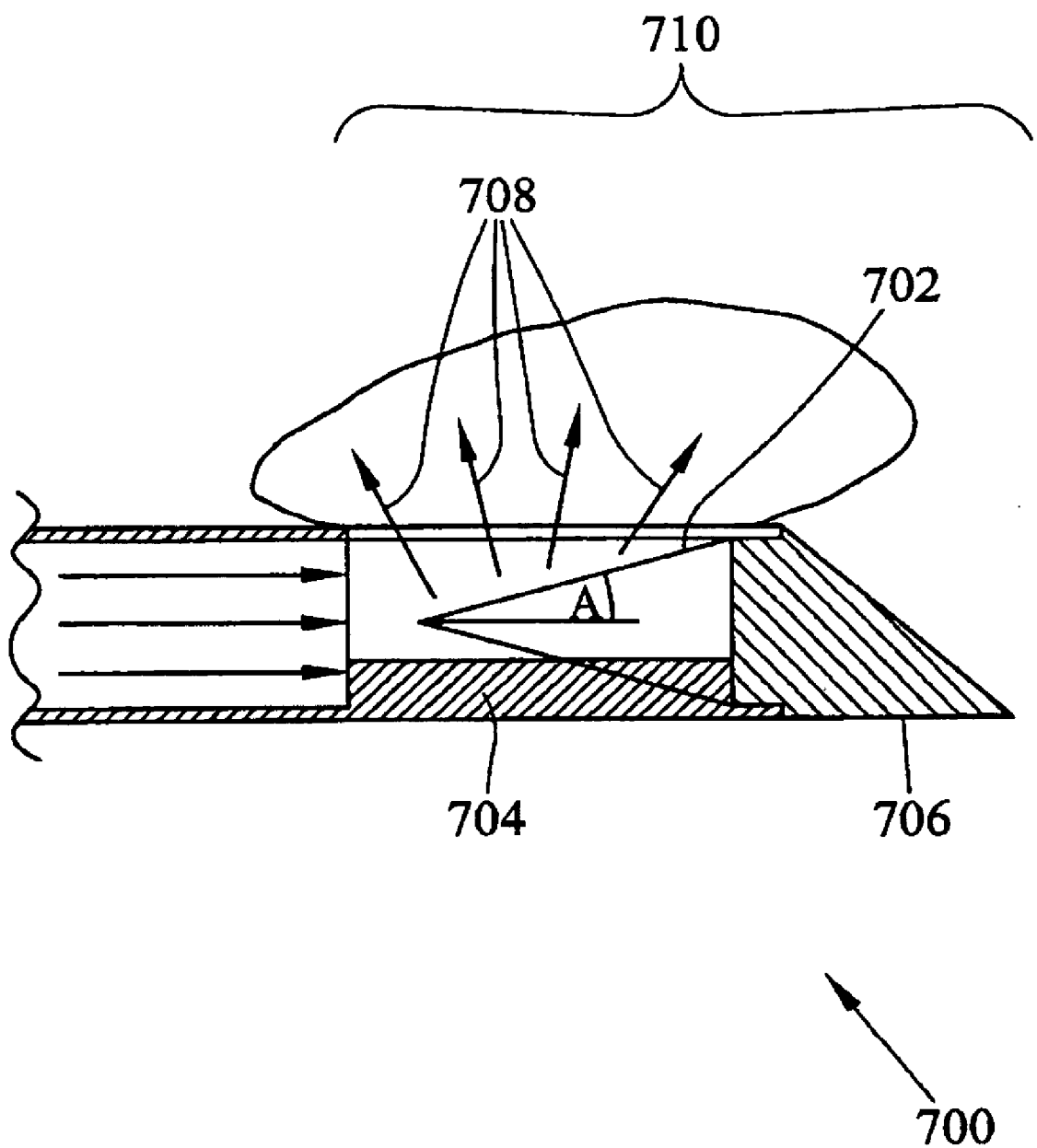
FIG. 7 is a cross-section view of another exemplary embodiment of a radiation needle device and an attached dispersion assembly.

FIG. 7 shows a radiation needle 700 having a conical fluorescent target 702, a shaping shield 704, and a penetration tip 706. Shaping shield 704 can shield the body from a portion of secondary x-rays 708. This shielding can be useful if dispersion assembly, generally designated 710, is placed near a tumor rather than inside a tumor. In another embodiment, radiation shaping shield 704 can block some of secondary x-rays 708, reducing the intensity of secondary x-rays 708 that are emitted from dispersion assembly 710. This feature can be useful if radiation needle 700 is inserted into a tumor, but closer to one side of the tumor than another. Radiation shaping shield 704 is composed of essentially the same materials as radiation needle 700. The thickness required for shielding secondary x-rays 708 of various energies is provided in Table 2.

Referring to FIG. 7, penetration tip 706 can be sharpened and rigid enough to puncture tissue. In another embodiment, the hole through which a radiation needle (such as radiation needle 700) is inserted can be created by any alternate means known to those skilled in the art of surgery, and then radiation needle 700 can be inserted into the hole. In such a case, penetration tip 706 need not be especially sharp.

X-Ray Spectrum of the Secondary X-Rays

The x-ray spectrum of the secondary x-rays (such as secondary x-rays 410 shown in FIG. 4) can be determined by the spectrum of primary x-rays (such as primary x-rays 408 shown in FIG. 4) and the composition of a fluorescent target (such as fluorescent target 416 shown in FIG. 4). Primary x-rays 408 incident upon fluorescent target 416 can be absorbed and cause secondary x-rays 410 due to fluorescence. A small fraction of primary x-rays 408 are typically not absorbed by fluorescent target 416, but instead are scattered and diffracted and added to secondary x-rays 410. These diffracted and scattered x-rays can contribute to secondary x-rays 410, but not significantly. The majority of secondary x-rays 410 are due to x-ray fluorescence of fluorescent target 416. Fluorescent secondary x-rays 410 are of lower energies than primary x-rays 408. Diffraction contributes at specific directions based on the crystal structure of the target according to Bragg's Law:

$$n\lambda = 2d \sin \Theta$$

Bragg's Law depends on the wavelength of the incident radiation ($\lambda$), the lattice parameter of the fluorescent target's structure ($d$), the angle the incident radiation makes with the fluorescent target ($\Theta$), and the number of crystal layers through which the x-rays are diffracted (n). The secondary radiation has the same wavelength and energy spectrum as the incident or primary radiation.

In order to maximize the generation of secondary x-rays at the highest possible energy level, the materials for the anode (such as anode 206 shown in FIG. 2) of the x-ray generator (such as x-ray generator 102 shown in FIGS. 1 and 2) and the fluorescent target (such as fluorescent target 416 shown in FIG. 4) can be selected to have Kα energy levels that are close to each other with fluorescent target having a slightly lower Kα energy level than the anode material of the x-ray generator. Therefore, the peak energy index ratio, the ratio of the energy of secondary x-rays 410 to the energy of primary x-rays 408, can be close to 1. In this embodiment, primary x-rays 408 at the Kα energy having a high intensity fluorescent target 416 and create secondary x-rays 410 at the Kα energy of the target, maximizing the intensity of the delivered dose. The Kα energies of some exemplary embodiments of fluorescent target 416 are shown below in Table 3. Though it is not necessary for the Kα peak of anode 206 to be at a higher energy than the Kα peak of fluorescent target 416, this can be the case in order to increase the total intensity of primary x-rays 408 and subsequently the intensity of secondary x-rays 410.

Penetration of Secondary X-Rays into Tissue

Calculating the absorption of different energies of low energy x-rays is important in configuring radiation delivery system to selectively irradiate only the volume of a targeted tumor while minimizing the irradiation of nearby normal tissue. The linear absorption coefficient $\mu$ ($cm^{-1}$) of the target tissue can be calculated using the equation for $\mu$ described hereinabove. Absorption is specific to the tissue material and the energy of the radiation being absorbed. The depth of penetration of secondary x-rays 410 can be controlled by varying the material of the fluorescent target (such as fluorescent target 416 shown in FIG. 4), and subsequently the energy of secondary x-rays 410, allowing selection of treatment penetration depth for each patient based on a determination or estimate of neoplasm thickness. A controllable penetration depth allows neoplastic tissue irradiation while minimizing irradiation of nearby or underlying normal tissues. The mass absorption coefficients for Table 3 below can be interpolated from data available from the National Institute of Standards and Technology (NIST) (located at Gaithersburg, Md., U.S.A.). Soft tissue can be assumed to be composed of hydrogen (H), carbon (C), nitrogen (N), and oxygen (O) in quantities specified by the International Commission on Radiation Units and Measurements (ICRU) (located at Bethesda, Md., U.S.A.).

The half value layer (HVL) of radiation in a material is the depth at which fifty percent of the radiation is absorbed ($i/i_o$=0.5). Table 3, shown below, summarizes the linear half value layers in soft tissues for the Kα energies of various fluorescent target materials.

TABLE 3

Table of Linear Absorption Values and Half Value Layers for Various Fluorescent Target Materials

| Fluorescent Target Material | Kα Energy (keV) | M ($cm^2$/g) Soft Tissue | HVL Soft Tissue (mm) |
|---|---|---|---|
| Ti | 4.50 | 61.5 | 0.11 |
| Fe | 6.40 | 21.7 | 0.32 |
| Cu | 8.04 | 10.3 | 0.67 |
| Mo | 17.50 | 1.26 | 5.5 |
| Ag | 22.16 | 0.727 | 9.5 |
| Sn | 25.27 | 0.589 | 11.8 |
| Te | 27.47 | 0.491 | 14.1 |
| Ba | 32.19 | 0.355 | 19.5 |
| Ta | 57.52 | 0.210 | 33.0 |

As shown in Table 3, the linear half value layers in soft tissues span a significant range, but have a limited upper bound. Therefore, the maximum treatable volumes will be similarly restricted, and consequently, large tumor masses would require multiple insertions and treatments. It is important to note that the calculated values shown in Table 3 are for linear absorption in tissue. Secondary x-rays deposited from fluorescent target are also reduced by the inverse square of the distance from the fluorescent target.

According to one embodiment for treating a brain tumor approximately 2 centimeters in diameter, a radiation delivery system (such as radiation delivery system 100 shown in FIG. 1) is provided having a radiation needle (such as radiation needle 400 shown in FIG. 4) with an outside diameter of approximately 3 millimeters and a cylindrically-shaped hollow interior (such as interior 404 shown in FIG. 4) with a diameter of approximately 1 millimeter. The radiation delivery system can have a fluorescent target of tin (Sn) with a Kα characteristic radiation 25.27 keV for providing secondary radiation with approximately 50% that is determined, based on the above, to be absorbed in 1.2 centimeters of soft tissue. Therefore, based on the above, the radiation setting for a radiation delivery system can be set to irradiate only the target tissue with an appropriate margin to ensure complete tumor irradiation.

Another preferred embodiment of a fluorescent target having an angled surface similar to fluorescent target 502 (FIG. 5) for receiving primary x-rays 508 (FIG. 5). In this embodiment, the radiation beam can be generated by a PHILIPS® PW 1830 x-ray generator with an output voltage of 10–60 kV and a beam current of 10–60 mA. To detect the secondary x-rays, an AMPTEK® Silicon XR-100CR detector was used in conjunction with an AMPTEK® model PX2T/CR power supply and amplifier, both available from Amptek Inc. of Bedford, Mass., U.S.A. The AMPTEK® Silicon XR-100CR detector allows 200 eV energy resolution. An ORTEC® 916A multi-channel analyzer emulator and the MAESTRO®-32 MCA emulator software (both available from Oak Ridge Technical Enterprises Corporation of Oak Ridge, Tenn., U.S.A.) can be used to collect and analyze the data from the detector.

The x-rays produced from an x-ray generator having a copper anode were used to fluoresce iron in a steel fluorescent target (such as target 502 shown in FIG. 5). Copper Kα radiation has a characteristic energy of 8.04 keV and iron Kα radiation has a characteristic energy of 6.40 keV. In other embodiments, radiation from a tungsten anode can be used to fluoresce a number of different target materials including tantalum (Ta), molybdenum (Mo), silver (Ag), tin (Sn), and copper (Cu).

Figure 8:
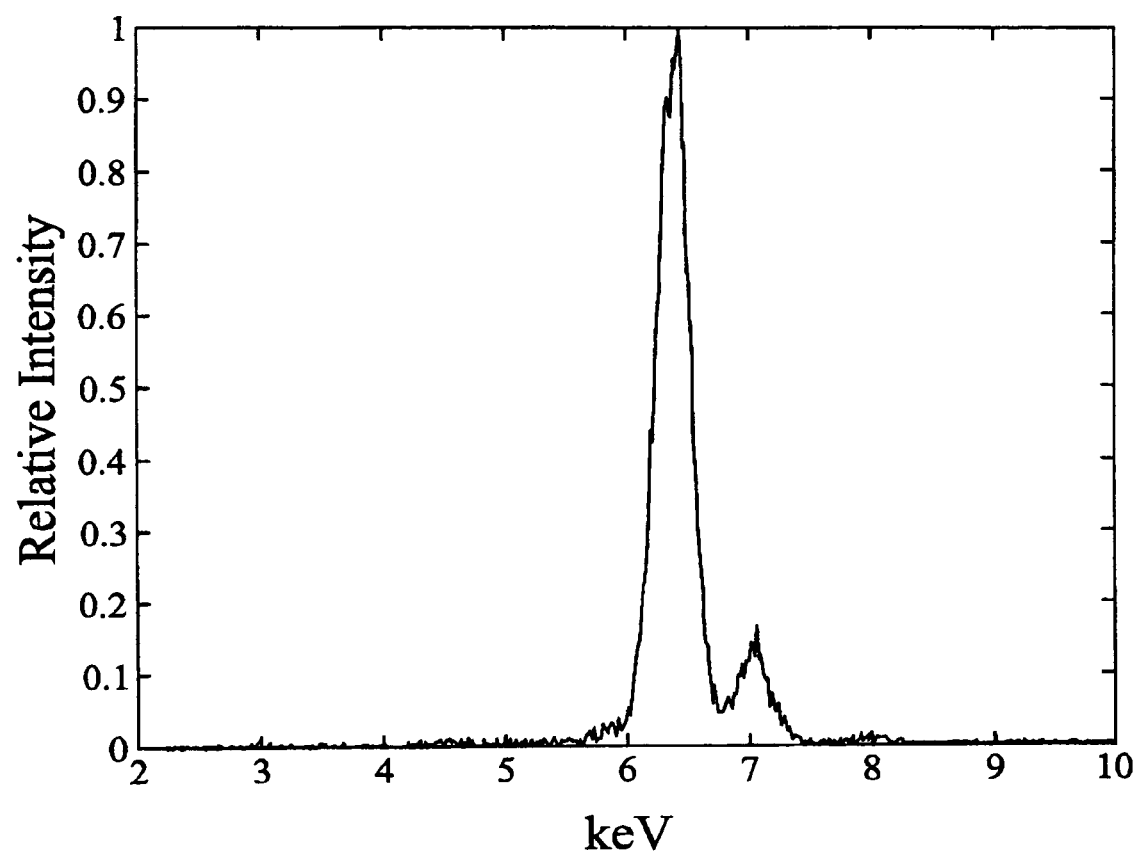
FIG. 8 is a chart of the fluorescent radiation spectrum of a steel sample.

FIG. 8 illustrates a chart of the fluorescent radiation spectrum of a steel sample. Using a pinhole beam, this spectrum was taken with the detector mounted normal to the steel surface and with the target surface fixed at 45 degrees to the incident beam. The radiation is nearly monochromatic at two closely related peaks. The larger of the two is the iron Kα peak at 6.40 keV while the smaller one is the iron Kβ peak at 7.06 keV. Fluorescent radiation consists of one or more monochromatic peaks, which makes it possible to determine treatment depth accurately. Results indicate that fluorescent radiation is emitted across the full quadrant scanned.

Figure 9:
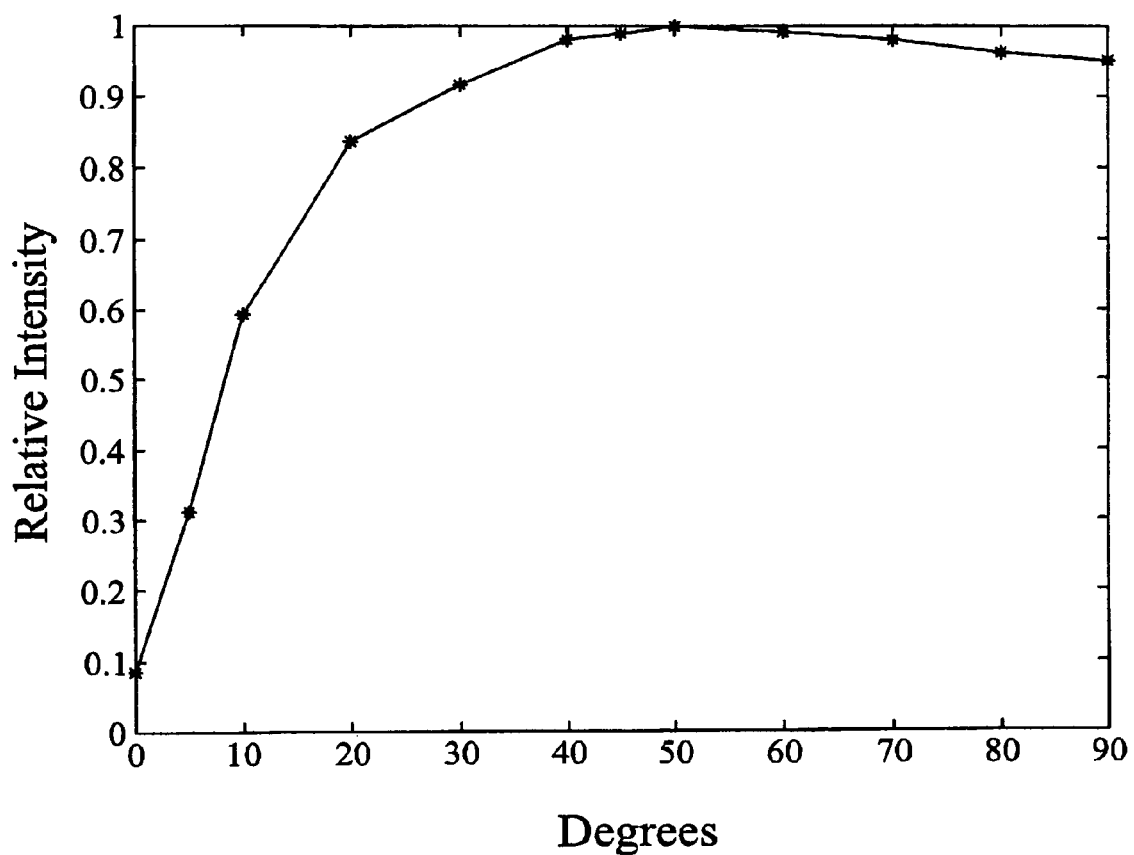
FIG. 9 is a chart of relative intensity versus degrees from the plane of fluorescence for a steel plane fluoresced with copper Kα radiation.

FIG. 9 illustrates a chart of relative intensity versus degrees from the plane of fluorescence for a steel plane fluoresced with copper Kα radiation. The results were obtained when a detector was positioned 2 centimeters away from the center of the plane of fluorescence and when a steel sample was positioned at a 45 degree angle to the incident beam. Higher energy radiation can be used to obtain linear half value layers in soft tissue of up to 3 cm. On the horizontal axis, the number of degrees is measured from the plane of the steel (i.e., 90 degrees is normal to the plane of the dispersive element). For angles greater than 40 degrees, the relative intensity drops. This is partly due to the fact that the detector window is not just a point, but has an area of 13 mm². It is also due to the fact that the beam fluoresces an area of the steel and not just a point.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A device for irradiating a portion of a body, said device comprising:
(a) a rigid hollow radiation needle, said rigid hollow radiation needle having at least one rigid radiation conduit, said rigid radiation conduit having a first end and a second end, wherein said rigid radiation conduit is operable to pass primary x-rays from said first end to said second end, said primary x-rays being generated by an x-ray generator, said x-ray generator being external to said body, said x-ray generator being operably connected to said first end to pass said primary x-rays to said second end by means of said rigid radiation conduit, said rigid radiation conduit in said rigid hollow radiation needle having an internal diameter between one centimeter and 0.1 millimeters, said rigid hollow radiation needle having a length, said length being between 2 centimeters and 75 centimeters;
(b) a fluorescent target connected to said second end of said rigid radiation conduit and positioned to absorb said primary x-rays passed to said second end to produce by fluorescence secondary x-rays for irradiating a predetermined portion of said body, said fluorescent target comprises at least one element having an atomic number that is one of 75–79 and 81, said fluorescent target having a shape, said shape having an essentially spherically-shaped surface, said surface absorbing a fraction of said primary x-rays whereby said fluorescent target is caused to fluoresce and to emit said secondary x-rays, said secondary x-rays and said primary x-rays being related by a peak energy index ratio between 0.01 and 1; and
(c) an x-ray transmitting window positioned adjacent to said fluorescent target, said secondary x-rays exiting said rigid hollow radiation needle through said x-ray transmitting window, said secondary x-rays irradiating a volume, said volume conforming to a predetermined portion of a target tissue within said body, said volume being between one tenth of a cubic millimeter and 115 cubic centimeters whereby said tissue is therapeutically irradiated by said secondary x-rays.

2. A device for irradiating a portion of a body, said device comprising:
(a) a rigid hollow radiation needle, said rigid hollow radiation needle having at least one rigid radiation conduit, said rigid radiation conduit having a first end and a second end, wherein said rigid radiation conduit is operable to pass primary x-rays from said first end to said second end, said primary x-rays being generated by an x-ray generator, said x-ray generator being external to said body, said x-ray generator being operably connected to said first end to pass said primary x-rays to said second end by means of said rigid radiation conduit, said rigid radiation conduit in said rigid hollow radiation needle having an internal diameter between one centimeter and 0.1 millimeters, said rigid hollow radiation needle having a length, said length being between 2 centimeters and 75 centimeters;
(b) a fluorescent target connected to said second end of said rigid radiation conduit and positioned to absorb said primary x-rays passed to said second end to produce by fluorescence secondary x-rays for irradiating a predetermined portion of said body, said fluorescent target comprises at least one element having an atomic number that is one of 75–79 and 81 and another element having an atomic number of 80, said fluorescent target having a shape, said shape having an essentially spherically-shaped surface, said surface absorbing a fraction of said primary x-rays whereby said fluorescent target is caused to fluoresce and to emit said secondary x-rays, said secondary x-rays and said primary x-rays being related by a peak energy index ratio between 0.01 and 1; and
(c) an x-ray transmitting window positioned adjacent to said fluorescent target, said secondary x-rays exiting said rigid hollow radiation needle through said x-ray transmitting window, said secondary x-rays irradiating a volume, said volume conforming to a predetermined portion of a target tissue within said body, said volume being between one tenth of a cubic millimeter and 115 cubic centimeters whereby said tissue is therapeutically irradiated by said secondary x-rays.

3. A device for irradiating a portion of a body, said device comprising:
(a) a rigid hollow radiation needle, said rigid hollow radiation needle having at least one rigid radiation conduit, said rigid radiation conduit having a first end and a second end, wherein said rigid radiation conduit is operable to pass primary x-rays from said first end to said second end, said primary x-rays being generated by an x-ray generator, said x-ray generator being external to said body, said x-ray generator being operably connected to said first end to pass said primary x-rays to said second end by means of said rigid radiation conduit, said rigid radiation conduit in said rigid hollow radiation needle having an internal diameter between one centimeter and 0.1 millimeters, said rigid hollow radiation needle having a length, said length being between 2 centimeters and 75 centimeters;
(b) a fluorescent target connected to said second end of said rigid radiation conduit and positioned to absorb said primary x-rays passed to said second end to produce by fluorescence secondary x-rays for irradiating a predetermined portion of said body, said fluorescent target comprises at least one element having an atomic number that is one of 11, 12, 13, 14, 19–35, 37–42, 44–52, 55, 56, and 72–74 and another element having an atomic number of 80, said fluorescent target having a shape, said shape having an essentially spherically-shaped surface, said surface absorbing a fraction of said primary x-rays whereby said fluorescent target is caused to fluoresce and to emit said secondary x-rays, said secondary x-rays and said primary x-rays being related by a peak energy index ratio between 0.01 and 1; and (c) an x-ray transmitting window positioned adjacent to said fluorescent target, said secondary x-rays exiting said rigid hollow radiation needle through said x-ray transmitting window, said secondary x-rays irradiating a volume, said volume conforming to a predetermined portion of a target tissue within said body, said volume being between one tenth of a cubic millimeter and 115 cubic centimeters whereby said tissue is therapeutically irradiated by said secondary x-rays.

* * * * *